(12) United States Patent
Spencer et al.

(10) Patent No.: US 11,378,495 B2
(45) Date of Patent: Jul. 5, 2022

(54) METHODS, SYSTEMS AND DEVICES FOR AGENT DETECTION

(71) Applicant: Georgia Tech Research Corporation, Atlanta, GA (US)

(72) Inventors: Thomas Spencer, Atlanta, GA (US); David Hu, Atlanta, GA (US); Alexander B. Lee, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 751 days.

(21) Appl. No.: 16/265,923

(22) Filed: Feb. 1, 2019

(65) Prior Publication Data

US 2019/0234841 A1  Aug. 1, 2019

Related U.S. Application Data

(60) Provisional application No. 62/624,939, filed on Feb. 1, 2018.

(51) Int. Cl.
| | |
|---|---|
| *G01N 1/24* | (2006.01) |
| *G01N 1/14* | (2006.01) |
| *G01N 33/00* | (2006.01) |
| *G06N 20/00* | (2019.01) |
| *G01N 1/22* | (2006.01) |

(52) U.S. Cl.
CPC .............. *G01N 1/24* (2013.01); *G01N 1/14* (2013.01); *G01N 1/2273* (2013.01); *G01N 33/0062* (2013.01); *G01N 33/0073* (2013.01); *G06N 20/00* (2019.01); *G01N 2033/0068* (2013.01)

(58) Field of Classification Search
None
See application file for complete search history.

(56) References Cited

U.S. PATENT DOCUMENTS

| 6,234,006 B1 * | 5/2001 | Sunshine | G01N 33/0009 73/29.01 |
|---|---|---|---|
| 2003/0127105 A1 * | 7/2003 | Fontana | A45D 33/26 132/200 |
| 2010/0229658 A1 * | 9/2010 | Glezer | G01N 1/2273 73/863.81 |

OTHER PUBLICATIONS

Brauns, et al., "Temperature Modulation of a Catalytic Gas Sensor," Oct. 2014, Sensors , vol. 14, No. 11, pp. 20372-20381.
Catania, "Underwater 'Sniffing' by Semi-Aquatic Mammals," Dec. 28, 2006, NATURE, vol. 444 pp. 1024-1025.
Chinh et al., "NO Gas Sensing Kinetics at Room Temperature Under UV Light Irradiation of In2O3 Nanostructures," Oct. 2016, Sci. Rep., vol. 6, p. 35066.
Ivlev, et al., "The Use of Olfaction by the Russian Desman (*Desmana moschata* L.) During Underwater Swimming," Sep. 2013 Doklady Biological Sciences pp. 280-283.

(Continued)

*Primary Examiner* — Daniel S Larkin
(74) *Attorney, Agent, or Firm* — Troutman Pepper Hamilton Sanders LLP; Ryan A. Schneider

(57) ABSTRACT

Methods, systems, and devices that takes advantage of the unique fluid dynamics involved when oscillating flow across a sensor or sensor array. A time-variant source of information about an agent(s) of interest being sensored is established. This source of information is used in machine learning algorithms to speed up the time and accuracy of agent classification and identification.

20 Claims, 4 Drawing Sheets

(56) References Cited

OTHER PUBLICATIONS

Figure 1:
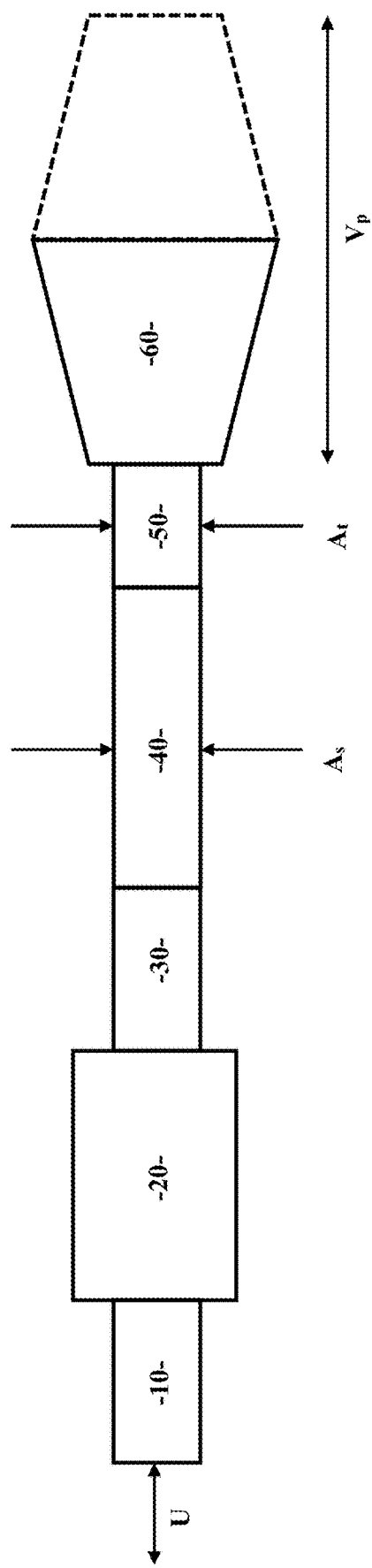

Kato, et al., "Temperature-Dependent Dynamic Response Enables the Qualification and Quantification of Gases by a Single Sensor," May 1997, Sens. Actuators B Chem., vol. 40, No. 1, pp. 33-37.
Kubersky et al., "Quantitative Fluctuation-Enhanced Sensing in Amperometric NO2 Sensors," Jul. 2015, Chem. Phys., vol. 456, pp. 111-117.
Kumar, et al., "UV-Activated MoS2 Based Fast and Reversible NO2 Sensor at Room Temperature," Nov. 2017, ACS Sens, vol. 2, No. 11, pp. 1744-1752.
Lee and Hu, "Bubble Stabilization by the Star-Nosed Mole," Dec. 6, 2018, American Physical Society, pp. 123101/1-123101/14.
Smulko et al., "New Approaches for Improving Selectivity and Sensitivity of Resistive Gas Sensors: A Review," 2015 Sens. Rev., vol. 35, No. 4, pp. 340-347.
Smulko and Trawka, "Gas Selectivity Enhancement by Sampling-And-Hold Method in Resistive Gas Sensors," Nov. 2015 Sens. Actuators B Chem., vol. 219, pp. 17-21.
Vergara, et al., "Optimized Feature Extraction for Temperature-Modulated Gas Sensors," vol. 2009 Journal of Sensors, 2009, pp. 1-10.
Ziyatdinov, et al., "Bioinspired early detection through gas flow modulation in chemo-sensory systems," Jan. 2015 Sens. Actuators B Chem., vol. 206, pp. 538-547.

\* cited by examiner

METHODS, SYSTEMS AND DEVICES FOR AGENT DETECTION

CROSS-REFERENCE TO RELATED APPLICATIONS

This Application claims priority to and benefit under 35 USC § 119(e) of U.S. Provisional Patent Application Ser. No. 62/624,939, filed 1 Feb. 2018, which is hereby incorporated by reference herein in its entirety as if fully set forth below.

STATEMENT REGARDING FEDERALLY SPONSORED RESEARCH OR DEVELOPMENT

This invention was made with government support under Award Nos. 1510884 and PHY-1255127 awarded by the National Science Foundation. The government has certain rights in the invention.

BACKGROUND OF THE INVENTION

1. Field of the Invention

The present invention relates generally to detection methods, systems, and devices, and more particularly to methods, systems, and devices that temporarily increase the concentration of target agents, for example particles, in proximity to a sensor thereby improving agent detection and identification.

2. Description of Related Art

Conventional sensing technologies capable of detecting chemical, biological, radiological, and nuclear agents are limited by range, volume, and environment. Agencies within the Department of Defense (DoD) and the Department of Homeland Security, such as Edgewood Chemical Biological Center, Defense Threat Reduction Agency, U.S. Coast Guard, and U.S. Customs and Border Protection, rely on sensors to protect people, animals, and food products from contamination and to impede drug trafficking and smuggling of banned items. In many cases, sensors are used for early detection of possible chemical/biological agents, providing early warning of these threats. However, as good as conventional sensor technology has become, there are still significant limitations that hinder security and military operations.

For example, ion and mass spectrometry separates ions based on their mobility and mass-to-charge ratio and can detect trace amounts of fentanyl wiped off a surface. Colorimetric sensor arrays change color when exposed to chemical aerosols, and microcantilever devices produce a measurable deflection due to the gas causing a chemical reaction, surface stress, or resonant frequency change. For liquids, methods such as fluorescence quenching for explosive detection and microfluidics for medical diagnosis have shown much promise.

Despite these advances, a universal challenge remains—these sensors are proximity limited. They must be placed close to the target chemical or the chemical must be placed directly on the sensor, and detection is only possible if the chemical is present in sufficient concentrations. This is a significant limitation of current sensing technology because the location and/or presence of target chemicals is often unknown, such as in the detection of narcotics at an airport or explosives in the field.

Moreover, a more advanced challenge is the detection of contaminants underwater, an application that would be useful for port and harbor security, pipeline management, and securing public drinking water. However, contaminants (such as chlorine and salt) present in liquids (i.e., drinking water and seawater) cause existing underwater sensors to degrade over time, requiring the sensor to be replaced or recalibrated.

With these challenges still outstanding, is thus an intention of the present invention to take significant innovative steps toward countering traditional limitations associated with sensors used for chemical detection. A biomimetic nose capable of detecting trace amounts of agents both in air and in liquids and at distances greater than currently possible is an object of the present invention.

BRIEF SUMMARY OF THE INVENTION

The present invention includes methods, systems, and devices that provide enhanced chemical detection and characterization. It employs machine learning algorithms to continually improve agent characterization and also mimics animal sniffing. Although conventional detection methods (e.g., long inhales or exposure to stagnant air) face limitations regarding sample proximity and sensing time, the present invention fills this gap.

In another exemplary embodiment, an attachment (end effector) allows for enhanced chemical detection underwater. Higher quality sensors can enhance machine olfaction. The present invention is a valuable, versatile tool for CBRN threat detection in air and underwater with applications ranging from military use (such as maritime and active combat operations) to critical infrastructure protection to general environmental monitoring.

Briefly described, in an exemplary form, the present invention is a device that takes advantage of the unique fluid dynamics involved when oscillating flow across a sensor or sensor array. The way in which a gas is moved across the sensors provides a new time-variant source of information about an agent(s) of interest in the gas, in many circumstances, air. This new source of information can be used in machine learning algorithms to speed up the time and accuracy of agent classification and identification.

This innovative feature does not rely on the sensor being completely reset between measurements, which allows for the possibility of continuous air monitoring. Such continuous monitoring can be used to identify when an environment has deviated from a prior steady-state level such as is the case when an unwanted agent enters the environment.

In exemplary embodiments, the agent(s) are chemicals and the gas sensed is air.

An attachment (end effector) to the device can be used to identify agents of interest in liquids with air monitoring sensors. The level of separation between the sensors and the liquid reduces the chance of biofouling. To provide a large enough sample volume of air, a bubble must be pushed into the liquid and then sucked back across the sensors. Therefore, the bubble must be stable in the liquid—not pinch off from the end effector.

A good application of this is in the collection of bacteria or other types of airborne biomass. Such airborne "particles" are able to be detected by microfluidic devices which need the bacteria to be suspended in a liquid. In such a case it is important to get the bacteria from the air onto a surface which can then be scrubbed off into a liquid for sensing once enough concentration has accumulated on the surface. The unique shape of the present invention's end effector (based off the star nose mole) can secure the bubble in place while keeping the maximum amount of surface area exposed to the liquid. The present invention preferably works with many types of sensor, not just metal oxide Figaro TGS 2610 chemical sensors used in in exemplary discussions of the invention.

In yet another exemplary embodiment, the technology of the present invention is used for the collection of (small) particles onto a substrate on the channel/tube wall. The same physical principles apply, but instead of there being an odor/chemical in the air (medium) that has to react on one or more sensors, the (small) particles "land" on a sensor more aptly called a "collector" in this embodiment. The size range for particles that this works best is approximately 10 micrometers or less in diameter.

Such small particles are light enough that they follow the air's flow profile in a very similar way that odor molecules do (after all, chemicals have mass albeit a very small amount). During the transition from inhalation to exhalation, the small particles in the air slow down and have time to diffuse onto a given section of the wall or collector located on the wall. Then when the air is moved again, the particles farther downstream get brought into the collection region and the process repeats.

The small odor/chemical molecules reach the sensor surface by following the flow and through diffusion. In such embodiments, the invention doesn't focus on sensing what the small particles in the air are (odor, chemicals, etc.), but focuses on collecting those particles on a specific surface (in chemical sensing that surface is a sensor).

In this application, the present invention is a system comprising a port in fluid communication with a medium containing an agent, a station in fluid communication with the port, and a medium oscillation source to impart an oscillating flow of the medium through the station, wherein the station comprises a collection station for the collection of an amount of the agent over cycles of oscillation.

In another exemplary embodiment, the present invention is an agent detection method comprising subjecting a sensor to oscillating flow of a medium containing an agent of interest, establishing a time-variant characteristic associated with the agent of interest from information received from the sensor, and detecting the agent of interest from evaluation of the time-variant characteristic.

The sensor can comprise a single sensor, multiple sensors, and/or an array of sensors.

The medium can be a gas or a liquid.

The agent of interest can be a chemical, or more than one chemical.

The method can further comprise employing one or more machine learning algorithms. The machine learning algorithm can be used to improve the speed of establishing the time-variant characteristic, and/or to improve the speed of detecting the agent of interest, and/or to improve the consistency of the oscillating flow.

The method can further comprise continuously subjecting, establishing and detecting for a predetermined time period without sensor reset during the predetermined time period.

The method can operate in a liquid, the method further comprises creating, in the liquid, a bubble of gas containing the agent of interest, and then subjecting the sensor to the oscillating flow of the gas in the bubble, wherein the bubble is stable in proximity to the sensor for a time sufficient to complete the step of subjecting the sensor to the oscillating flow.

In another exemplary embodiment, the present invention is a system for agent detection comprising a port in fluid communication with a medium containing an agent of interest, a sensor station in fluid communication with the port, a medium oscillation source to impart an oscillating flow of the medium through the sensor station, and a processor for establishing a time-variant characteristic associated with the agent of interest from information received from the sensor station, and detecting the agent of interest from evaluation of the time-variant characteristic.

The sensor station can comprise a single sensor, multiple sensors, and/or an array of sensors.

The medium can be selected from the group consisting of a gas and a liquid.

The agent of interest can be a chemical, or more than one chemical.

The processor can further employ one or more machine learning algorithms.

The present invention can be used in hospitals, which need to monitor if the air has changed to have something harmful in it. And in hydroponic greenhouses that need to know if something has happened to the interior air quality if something such as the door was left open and extraneous aerosols drifted in.

These and other objects, features and advantages of the present invention will become more apparent upon reading the following specification in conjunction with the accompanying drawing figures.

BRIEF DESCRIPTION OF THE DRAWINGS

FIG. 1 is a schematic of the present invention according to an exemplary embodiment.

FIG. 2 is a schematic of a mismatched sensor section and tubing illustrating potential issues with non-uniform cross-sectional flow.

FIG. 3 is a schematic of the present invention according to another exemplary embodiment, including an optional end effector for use in non-gaseous environments.

FIG. 4A is a photo of a star-nosed mole, and FIG. 4B is a photo of an exemplary end effector inspired by the star-nosed mole and other mammals that can smell underwater.

DETAIL DESCRIPTION OF THE INVENTION

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

Olfaction is defined as the chemoreception that forms the sense of smell. In 1964, the first device to perform olfaction was built using microelectrodes. The device was only capable of registering a change between differing volatiles. It could not classify or identify the odorant, which is the contemporary goal of machine olfaction.

In 1988, the term "electronic nose" was introduced at a conference in the U.K., and the term has evolved to include any device intended to detect odors using a sensor array. Current goals in the field of chemical detection include reducing device size, decreasing cost, enhancing sensitivity using multi-sensor arrays (such as those found in "nose-on-a-chip" technologies), and improving signal processing.

Work by scientists at both the National Institute of Standards and Technology and the Food and Drug Administration has focused on improving the detection sensitivity of sensors by replicating the mechanism seen in canine sniffing.

In an exemplary embodiment of the present invention, improved sniffing technology is combined with machine learning, developing an innovative type of biomimetic nose, which features enhanced sensitivity for applications in both air and underwater. The present invention incorporates a pre-concentrator and is capable of improving the sensitivity of detecting airborne particles, such as TNT, PETN, and RDX from explosives, lending itself to DoD- and DHS-relevant applications.

A review of studies regarding mammalian olfaction revealed that mammals sniff at a frequency ranging from 2 to 10 hertz (Hz). Therefore, the present invention attempts to mimic this range and can be set to sniff at a specific frequency. To mimic the mechanics of a sniff, a 3-D printed diaphragm pump resembling a bellows was developed, making the motion of air repeatable and controllable, evacuating the bellows by moving air at a specific velocity and frequency.

FIG. 1 is a schematic of the present invention according to an exemplary embodiment. A medium oscillation source, which can be a pump 60 draws ambient environment at velocity U in and out of a port in fluid communication with a medium containing an agent of interest. Such an oscillating flow can enter tubing 10. The tubing may be a single, unitary design from ambient to pump (where elements 10, 20, 30, 40, 50 comprise the tubing), or can include separate sections as designated, as long as fluid communication is available from inlet/outlet (the port) of the tubing section 10 to the pump 60.

A sample section 20 is illustrated, as is a sensor section 40. The sensor section 40 can comprise one or more sensors. In exemplary embodiments, the fluid communication/path between, for example, sections 30, 40 and 50 are smooth transitions, if not of uniform cross-sectional area (preferably diameter) to avoid unintended, "trapped" or "old" agents.

Figure 2:
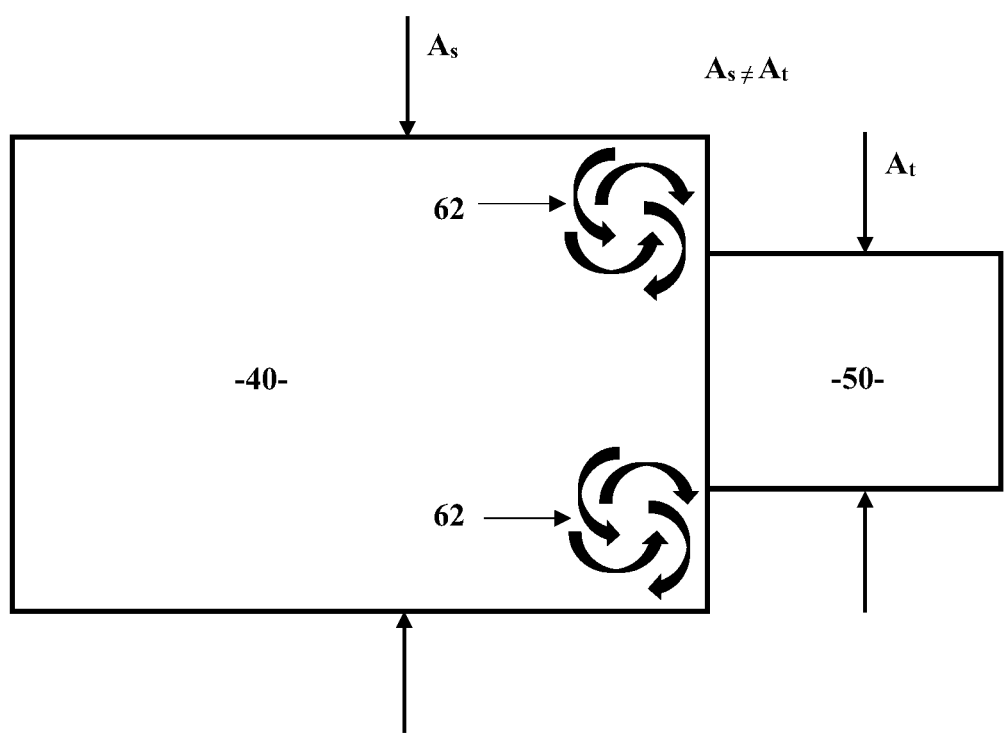

For example, preferably cross-sectional area (if circular tubing is used, diameter) $A_s=A_t$. If there is a large enough deviation, those of skill in the art understand that, as shown in FIG. 2, trapped or old agent 62 (prior air or liquid samples) can remain in the sensor section 40, providing erroneous results.

In an exemplary embodiment, given the cross-sectional area of the tubing, $A_t$, the corresponding equation is:

$$\Delta V = \frac{UA_t}{f} \quad (1)$$

where $\Delta V$ is the volume change of the pump/bellows 60, U is the desired air or other fluid/liquid speed, and f is the desired frequency of sniffing. For initial testing, the present invention was set to mimic the frequency/velocity of a dog's sniff—a frequency of 5 Hz and velocity of 1.5 meters per second (m/s).

The pump 60 can oscillate the medium containing an agent of interest at a desired speed, for example, air at a speed of up to 5.5 m/s and within the aforementioned frequency range. The section 20 for the sample requiring detection and a previously calibrated metal oxide sensor of sensor section 40 are in fluidic series with the pump 60. The entire system can be controlled by microcontrollers and computer programs, as shown in FIG. 3.

In one exemplary embodiment, while U for dogs is approximately, 1.5 m/s, the present invention was set from approximately 0.5-5 m/s. While the sniff frequency f for dogs is approximately 5 Hz, the present invention was set to run at from approximately 0.2-10 Hz. The sensor container 40 cross sectional area, $A_s$ was approximately 0.07 cm$^2$. The tubing cross sectional area was substantially uniform, $A_s=A_t$. The pump volume change $V_p$ was thus in one exemplary instance manipulatable in a range from approximately 0.35 cm$^3$—approximately 17.5 cm$^3$.

Figure 3:
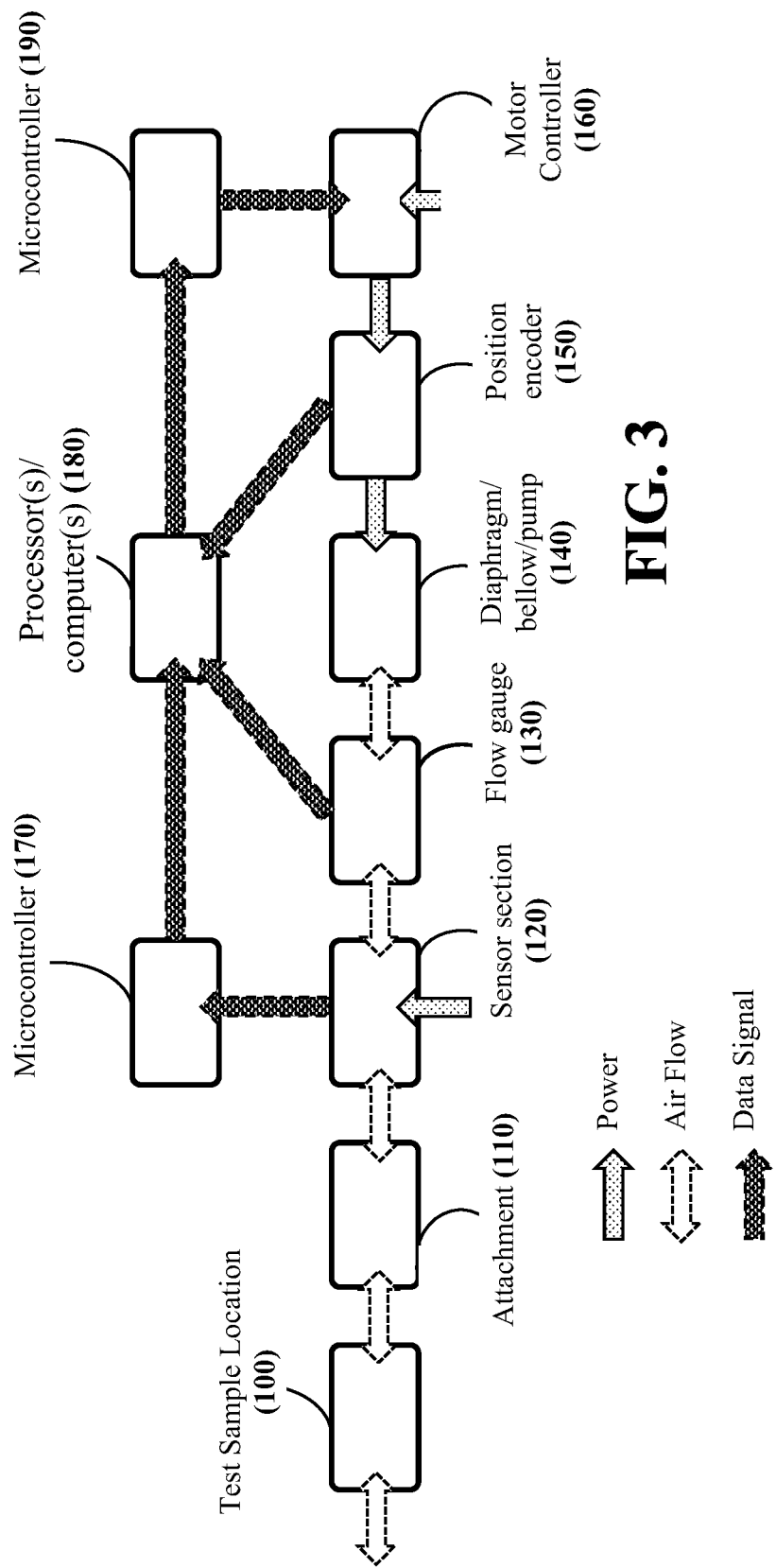

The invention as illustrated in FIG. 3 shows a power, air flow and data diagram, where the test sample is located at 100, a sensor section 120, a wind (medium/fluid) flow gauge 130, medium oscillation source, for example, a diaphragm/bellow/pump 140, position encoder 150, motor controller 160, microcontroller 170, processor (one or more processors and/or one or more computers) 180 and microcontroller 190.

An exemplary power supply to the sensor section 120 is 9V, and to motor controller 160 is 12 V. Power is provided to the position encoder 150 and the pump 140. Data is transmitted between microcontrollers 170, 190, processor (s)/computer(s) 180, gauge 130 and position encoder 150. Fluid communication is provided through sample 100, sensor section 120, gauge 130, and pump 140.

The present invention's improved sensing is thought to be a benefit from "sniffing," that sniffing can temporarily increase the concentration of the agent/target particles.

In a conventional sensing system, air is either stagnant or moved quickly across the sensors causing a decrease in pressure. Both possibilities are disadvantageous to sensing, but sniffing can avoid this problem. The transition from inhalation to exhalation in sniffing causes fluids (e.g., air and water) to reverse direction, creating a brief spike in internal pressure. This pressure brings the chemical molecules closer together, maximizing their number in the detection volume of the sensor.

Moreover, larger particles respond less to these pressure fluctuations because it takes a greater force to overcome the inertia of such particles. Therefore, sniffing affords the ability to perform particle size discernment whereas traditional sensing systems rely on chemical reactions alone. To take advantage of the brief period (the time between inhalation and exhalation) of high particle count, the present invention needs to adapt and learn, which was created utilizing machine learning.

Machine learning allows computers to find their own solutions to problems without the programmer writing the solutions out. This can be done by separating complex tasks into simpler tasks that the computer can handle, such as grouping things based on a set of metrics. For example, humans categorize produce as vegetables or fruits—a delineation based on the sugar content of food.

Similarly, in machine olfaction, the one or more processors or computers are tasked with establishing a time-variant characteristic associated with the agent of interest from information received from the sensor station and detecting the agent of interest from evaluation of the time-variant characteristic.

In essence, the processor(s)/computer(s) computer is/are presented the task of identifying various odors. To accomplish this task, program(s) group data points based on a set of metrics. However, a central challenge of machine olfaction is in identifying one or more metrics, referred to herein as "characteristics" and/or "features," based on the data collected.

As the present invention "sniffs," the odorants displace oxygen directly atop the one or more sensors, in turn changing the voltage of the sensor(s). These voltage readings on their own are of little use. Instead, relevant features must be measured from them. In the produce example, the relevant "feature" was the sugar content of the produce. During recent testing of the invention, a signature unique to each type of cheese was derived from three characteristics or features: (i) the rate at which the voltage readings change, (ii) the variation in these changes, and (iii) the rate at which the odorant was expelled from the system. One or more of these are time-variant characteristics. And these characteristics allowed the present invention to group similar odors as coming from the same source. If each feature represents an axis in three-dimensional space, then various odor samples each can be assigned a position in space based on the present invention's measurements. A Nearest Neighbors algorithm was applied to group the samples based on their distance to other samples, and then a Support Vector Machine algorithm forms boundaries which establish the training data. Other machine learning techniques would also benefit from the addition of this additional feature.

This training data is the present invention's "life experience"—in other words, as the present invention is given a new sample, it can identify the source based on what it has previously identified. In testing, the present system proved to be a successful proof of concept, successfully distinguishing 83 percent of cheese pairings. Further research is needed to better distinguish between samples with nearly identical chemical compositions. The success rate can be improved by replacing the tested rather rudimentary sensor with a more advanced sensor or more than one sensors, such as microcantilever sensor(s) or a colorimetric sensor array.

Machine olfaction has generally been used for air/gas-based applications, but there are many potential applications for employing this technique underwater, including monitoring ship hulls, entrances to harbors, and within critical pipelines. However, several challenges exist with sensing in an all-liquid environment.

Figure 4A:

Specifically, submergence gives rise to unwanted biofilms that impede measurements, and overexposure to harsh chemicals requires sensor recalibration after only a few days of use. However, nature may offer solutions to overcoming these challenges. The present invention drew inspiration from several species of semi-aquatic mammals that can smell underwater: star-nosed moles (see, FIG. 4A), American water shrews, and Russian desmans. These mammals track the scent of their prey at the bottom of swamps by utilizing coordinated sniffing. They blow bubbles out their noses, quickly sucking them back in before the bubble can float away. The inhaled bubble is coated with molecules of the target smell, enabling the animal to pinpoint the target's location.

Figure 4B:
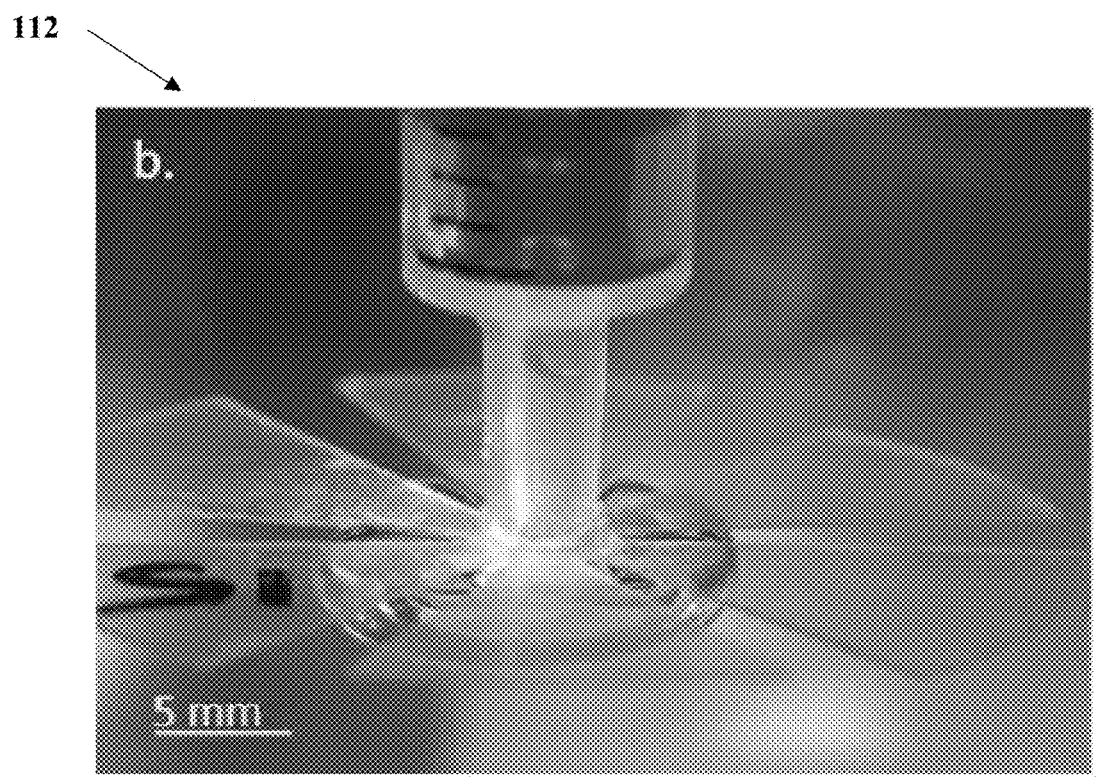

Based on the anatomy of the star-nose mole, the present invention can further comprise an attachment 110 (FIG. 3), for use with other elements of the present invention that can be submerged in a liquid without encountering the aforementioned challenges. How the unique shape of the star-nosed mole allows it to perform bubble-based sniffing was examined. Laser-cut plastic stars mimicking a mole nose was developed, and affixed them to syringes which, like the mole, blow bubbles underwater (see, FIG. 4B). By testing a range of "star" shapes, how the star shape prevents bubbles from escaping was elucidated: bubbles are stabilized by deformation by the "arms" of the star. As a mole blows a bubble, the bubble tries to rise through the gaps in the star while surface tension tries to minimize the bubble's surface area. Arms at a proper spacing cause a bubble to stay balanced on the star, even as the mole moves around during sniffing. The present invention (used in gas detection environments) was fitted with the plastic star shapes 112 and found that bubbles from multiple sniffs could be stabilized. Such star-shaped attachments 112 allows the present invention to stabilize bubbles long enough for chemicals to diffuse into them.

By mimicking the distinct shape of a mole nose, standard gas sensors can be employed rather than traditionally used sensors that must be immersed in a target liquid. The attachment 112 can be submerged, while still connected to the present invention stationed a distance away at a dry location. Together, these elements of the present invention are a first step in the design of an electronic nose capable of extended underwater detection.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. An agent detection method comprising:
   subjecting a sensor to a medium containing an agent of interest via an oscillating flow of the medium, oscillating between a flow into a port in fluid communication with the medium and a flow out of the port;
   establishing a time-variant characteristic associated with the agent of interest from information received from the sensor; and
   detecting the agent of interest from evaluation of the time-variant characteristic.

2. The agent detection method of claim 1, wherein subjecting the sensor to the oscillating flow comprises subjecting a single sensor to the oscillating flow.

3. The agent detection method of claim 1, wherein subjecting the sensor to the oscillating flow comprises subjecting more than one sensor to the oscillating flow.

4. The agent detection method of claim 1, wherein the medium is a gas.

5. The agent detection method of claim 1, wherein the medium is a liquid.

6. The agent detection method of claim 1, wherein the agent of interest is a chemical.

7. The agent detection method of claim 1 further comprising employing a machine learning algorithm.

8. The agent detection method of claim 1 further comprising employing a machine learning algorithm to improve the speed of detecting the agent of interest.

9. The agent detection method of claim 1 further comprising continuously subjecting, establishing and detecting for a predetermined time period without sensor reset during the predetermined time period.

10. The agent detection method of claim 1, wherein the medium is a liquid, and the method further comprises creating, in the liquid, a bubble of gas containing the agent of interest, and then subjecting the sensor to the oscillating flow of the gas in the bubble;
    wherein the bubble is stable in proximity to the sensor for a time sufficient to complete the step of subjecting the sensor to the oscillating flow.

11. A system comprising:
    a port in fluid communication with a medium containing an agent;
    a station in fluid communication with the port;
    a processor;
    memory in communication with the processor; and
    a medium oscillation source configured to subject the station to the medium containing the agent via an oscillating flow of the medium, oscillating between a flow into the port and a flow out of the port;
    wherein the memory stores instructions that, when executed by the processor, is configured to:
        establish a time-variant characteristic associated with the agent from information received from the station; and
        detect the agent from evaluation of the time-variant characteristic.

12. The system of claim 11, wherein the station comprises a collection station for the collection of an amount of the agent over cycles of oscillation.

13. The system of claim 11, wherein the agent is an agent of interest;
    wherein the station is a sensor station; and
    wherein the instructions are further configured to:
        establish the time-variant characteristic associated with the agent of interest from information received from the sensor station; and
        detect the agent of interest from evaluation of the time-variant characteristic.

14. The system of claim 13, wherein the sensor station comprises an array of sensors.

15. The system of claim 13, wherein the medium is selected from the group consisting of a gas and a liquid.

16. The system of claim 13, wherein the agent of interest is a chemical.

17. The system of claim 13, wherein the processor further employs a machine learning algorithm.

18. The system of claim 13, wherein the medium is a liquid; and
    wherein the medium oscillation source is further configured to:
        create, in the liquid, a bubble of gas containing the agent of interest;
        subject the sensor station to the oscillating flow of the gas in the bubble; and
        stabilize the bubble in proximity to the sensor station for a time sufficient to complete subjecting the sensor station to the oscillating flow of medium containing the agent.

19. An agent detection method comprising:
    creating, in a medium, a bubble of gas containing an agent of interest;
    subjecting a sensor to an oscillating flow of the gas in the bubble;
    establishing a time-variant characteristic associated with the agent of interest from information received from the sensor; and
    detecting the agent of interest from evaluation of the time-variant characteristic;
    wherein the bubble is stable in proximity to the sensor for a time sufficient to complete the step of subjecting the sensor to the oscillating flow.

20. The agent detection method of claim 19 further comprising continuously subjecting, establishing and detecting for a predetermined time period without sensor reset during the predetermined time period.

* * * * *